(12) United States Patent
Knowles

(10) Patent No.: US 8,571,809 B2
(45) Date of Patent: Oct. 29, 2013

(54) APPARATUS FOR CALCULATING SCORES FOR CHAINS OF SEQUENCE ALIGNMENTS

(75) Inventor: Gregory P. Knowles, Fortitude Valley (AU)

(73) Assignee: Bio informatics Systems Ltd. (HK)

( * ) Notice: Subject to any disclaimer, the term of this patent is extended or adjusted under 35 U.S.C. 154(b) by 0 days.

(21) Appl. No.: 12/885,531

(22) Filed: Sep. 19, 2010

(65) Prior Publication Data

US 2012/0245852 A1  Sep. 27, 2012

Related U.S. Application Data

(62) Division of application No. 11/019,807, filed on Dec. 20, 2004, now abandoned.

(60) Provisional application No. 60/637,630, filed on Dec. 17, 2004.

(30) Foreign Application Priority Data

Dec. 19, 2003  (AU) ................................ 2003907016

(51) Int. Cl.
*G06F 19/10* (2011.01)
*G06F 19/00* (2011.01)

(52) U.S. Cl.
USPC .............................................. 702/20; 702/19

(58) Field of Classification Search
None
See application file for complete search history.

(56) References Cited

PUBLICATIONS

Holmes et al. (Annual Conference on Research in Computational Molecular Biology, Proceedings of the Second Annual International Conference on Computational Molecular Biology (1998), pp. 102-108).*
Myers and Miller (Proceedings of the 6th Annual ACM-SIAM, Symposium on Discrete Algorithms (1995) pp. 38-47).*

* cited by examiner

*Primary Examiner* — Lori A Clow

(57) ABSTRACT

Each of a plurality of substantially co-linear alignments has a score. Each alignment may comprise a starting alignment that has been diagonally extended to meet a length requirement. Dynamic programming is performed in interalignment regions between the extended alignments to generate a corresponding set of interalignment scores. Alignment scores and interalignment scores are summed to generate a score for the entire chain of alignments. This process is repeated for multiple chains. Chains of alignments are ranked by chain score and are displayed to a user. In one embodiment, additional dynamic programming is performed at the head and tail of each chain to increase the chain score when possible. An integrated circuit that performs the method at high speed in hardware is disclosed. Techniques are disclosed that reduce the amount of interalignment dynamic programming. The method increases sensitivity and gives an order of magnitude speed improvement over NCBI-BLAST.

5 Claims, 15 Drawing Sheets

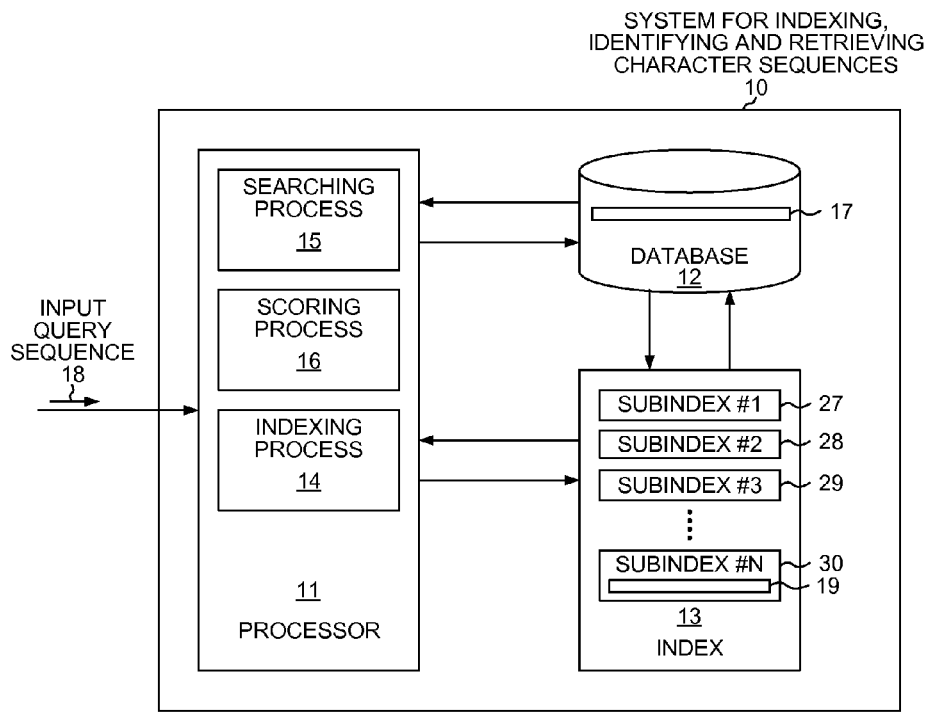

FIG. 1

```
n = index width
for m = 1 to (database_length-n)
    t = the n bases beginning at position m in the database
    -- Record pointer to this tuple
    if mostrecentoccurence[t] exists then
        update next occurrence pointer for mostrecentoccurence [t]
        to point to m
    else
        set first occurrence[t] = m
    end if
    -- Record the tuple
    write t, followed by a NULL pointer in the next occurrence field
    count[t] = count[t] + 1
    mostrecentoccurence[t] = m
next m
-- Write ancillary data structures
Write sequence descriptions and offsets
Write count[] array
Write firstoccurence[] array
```

FIG. 3

```
-----------------------------
-- Task 1: Find all diagonals
-----------------------------
n = index_width
max_step = minimum_match_length - index_width
for q = 1 to (query_length - n) step mex_step
    qt = the n bases beginning at position q in the query sequence
    m = firstoccurence[q]
    while m is not NULL
        t = the tuple at location m in the database index
        -- Try to non-gapped extend the tuple match at position m:q
        if try_extension(m,q) == GOOD then
            add diagonal(m,q) to diagonal tree
        end if
        -- See if there is another occurrence of this tuple
        m = next occurrence pointer at location m in the database index
    wend
next q
------------------------------------------
-- Task 2: Join nearby diagonals together
------------------------------------------
foreach diagonal in diagonal tree
    window := array of nearby diagonals to the "left" of diagonal
    bestneighbor := element of window which combined with diagonal gives
                    the best dynamic programming score
    if bestneighbor is not NULL then
        record that diagonal joins to bestneighbor on the left
    end if
    end foreach
end foreach
---------------------------------
-- Task 3: Render joined diagonals
---------------------------------
foreach diagonal in diagonal tree, starting from the "right most"
    render this diagonal
    left_diagonal := diagonal joined to the left of diagonal
    while left_diagonal is not NULL
        render the join region between diagonal and left_diagonal
        render left_diagonal
        -- See if left_diagonal joins to diagonals on its left
        left_diagonal := diagonal joined to the left of diagonal
    wend
    Output rendered hit
end foreach
```

FIG. 6

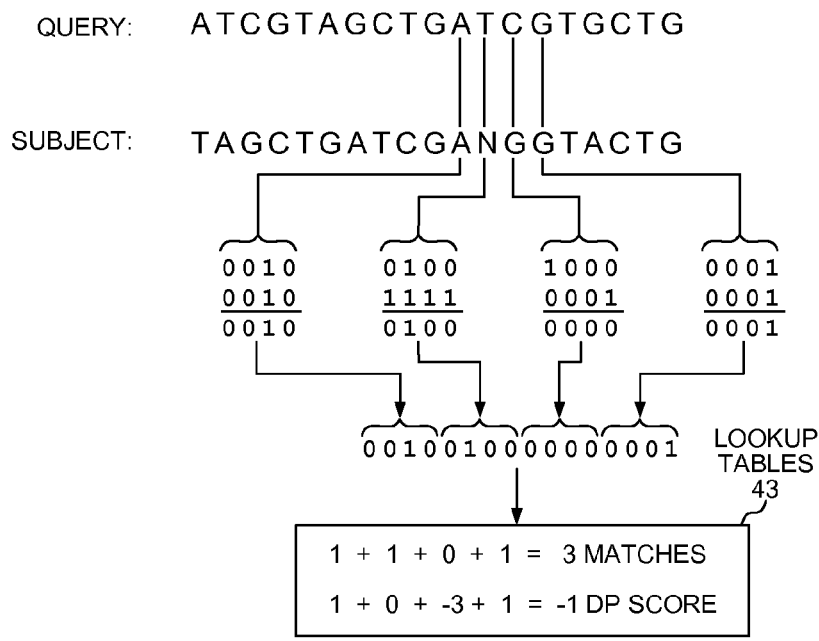

FIG. 7

>gnl|UG|Hs#S4066180    AGENCOURT_6580922    Homo sapiens    cDNA,    5'    end    /clone=IMAGE:5469280 /clone_end=5'/gb=BM554163/gi=18793524/ug=Hs.3216 77 /len=1396

Score = 396

Identities = 10/400 (2%)

Strand = Plus / Plus

Query: 4156  tggcctgggcgaagagggagag ... tcg 4213

Sbjct: 854   tgncctgggcgnnnnntnnnnn ... nnn 911

Query: 4214  attccccgagaaggaaaaggaa ... gga 4271

Sbjct: 912   nnnnnnnnnnnnnnnnnnnnnn ... nnn 969

⋮   ⋮   ⋮   ⋮   ⋮

Query: 4504  tcctcagctctcggcccatcgc ... cgc 4555

Sbjct: 1202  nnnnnnnnnnnnnnnnnnnnnn ... nnn 1253

FIG. 8

| BIT CLEAR IN BASE | P (MISMATCH) | % OF REWARD |
|---|---|---|
| 3 (A, C, G, T) | 3/4 | 100 |
| 2 (R, Y, M, K, S, W) | 1/2 | 50 |
| 1 (H, B, V, D) | 1/4 | 25 |
| 0 (N) | 0 | 0 |

FIG. 9

```
Score = 332

Identities = 367/367 (100%)

Strand = Plus / Plus

Query:  13   aaattctggtgactggcatagg ... atc  72

Sbjct:  1    aaattctggtgactggcatagg ... atc  60

Query:  73   aacaatgtcgccaaagcccatg ... acc  132

Sbjct:  61   aacaatgtcgccaaagcccatg ... acc  120

Query:  133  cgtgaaagcnatgatttatncc ... aga  191

Sbjct:  121  cgtgaaagcnatgatttatncc ... aga  179
         ⋮    ⋮                      ⋮    ⋮
Query:  369  aagtgtcctGC                     379

Sbjct:  357  aagtgtcctGC                     367
```

FIG. 10

APPARATUS FOR CALCULATING SCORES FOR CHAINS OF SEQUENCE ALIGNMENTS

CROSS REFERENCE TO RELATED APPLICATIONS

This application is based on and hereby claims priority under 35 U.S.C. §119 from Australian Provisional Application No. 2003907016, filed on Dec. 19, 2003, in Australia. This application also claims benefit under 35 U.S.C. §119 of U.S. Provisional Application No. 60/637,630, files Dec. 17, 2004, entitled "Indexing and Retrieving Character Sequences", by Knowles et al. This application is a Divisional of and claims priority under 35 U.S.C. §121 to application Ser. No. 11/019,807, filed on Dec. 20, 2004 now abandoned. The disclosure of the foregoing documents are incorporated herein by reference.

CROSS-REFERENCE TO COMPACT DISC APPENDIX

The Compact Disc Appendix, which is a part of the parent patent application Ser. No. 11/019,807 is one recordable Compact Disc (CD-R) containing information that is incorporated by reference in the disclosure of the present patent document. The Compact Disc contains hardware description in VHDL of an integrated circuit for carrying out a method of scoring chains of sequence alignments, in accordance with one specific embodiment of the present invention. The Compact Disc also contains source code for a multiclient software implementation that carries out a method of scoring chains of sequence alignments. A portion of the disclosure of this patent document contains material that is subject to copyright protection. All the material on the Compact Disc is hereby expressly incorporated by reference into the present application. The copyright owner of that material has no objection to the facsimile reproduction by anyone of the patent document or the patent disclosure, as it appears in the Patent and Trademark Office patent files or records, but otherwise reserves all copyright rights.

TECHNICAL FIELD

The present invention relates to identifying the similarity between character sequences, such as genomic and proteomic sequences. More specifically, the invention relates to finding a correlation between a query sequence of polynucleotide characters and sequences of polynucleotide characters from a DNA database, and to finding a correlation between a query sequence of amino acid characters and sequences of amino acid characters from a protein database.

BACKGROUND

The size of genomic sequence databases are currently growing at an exponential rate. Today, a typical genomic (DNA) database contains the sequence for billions of nucleotides. As a result, searching a genomic sequence database to find a sequence that correlates to an query sequence is often extremely computationally intensive.

Various sequence similarity searching algorithms are currently used to identify DNA and amino acid sequences within a genomic sequence database that have a correlation to a query sequence. Generally speaking, sequence searching algorithms may be classified as one of two types, namely global comparison methods and local comparison methods. Global comparison methods search a database sequence for the occurrence of an entire query sequence. Although such methods have a high degree of accuracy, they tend to be extremely slow. On the other hand, local comparison methods, such as NCBI-Blast and FastA, are faster than global comparison methods. Local comparison methods identify similar subsequences based on similar k-tuples of nucleic or amino acids.

Local comparison methods typically employ dynamic programming evaluations in order to find an optimal solution to a given search. Not surprisingly, the significant contributor to search time for such local comparison algorithms is the dynamic programming evaluations. Indeed, dynamic programming evaluations account for about 76% of the processing time of a typical NCBI-Blast search. Thus, although local comparison methods may be faster than global comparison methods, such methods are still quite computationally intensive.

A local comparison method is therefore sought that is less computationally intensive than methods such as NCBI-Blast and FastA. An apparatus is desired that performs a local comparison algorithm in less time than the search time of current searches employing local comparison methods.

SUMMARY

Each of a plurality of substantially co-linear alignments has a score. Each alignment may comprise a starting alignment that has been diagonally extended to meet a length requirement. Dynamic programming is performed in interalignment regions between the extended alignments to generate a corresponding set of interalignment scores. Alignment scores and interalignment scores are summed to generate a score for the entire chain of alignments. This process is repeated for multiple chains. Chains of alignments are ranked by chain score and are displayed to a user. In one embodiment, additional dynamic programming is performed at the head and tail of each chain to increase the chain score when possible. An integrated circuit that performs the method at high speed in hardware is disclosed. Techniques are disclosed that reduce the amount of interalignment dynamic programming. The method increases sensitivity and gives an order of magnitude speed improvement over NCBI-BLAST.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 1 is a high level block diagram of a system for indexing sequences including a processor with an indexing process and a searching process.

FIG. 3 is a pseudo-code listing for the indexing process of FIG. 1.

FIG. 4 shows hypothetical sequence SEQ ID No. 2.

FIG. 6 is a pseudo-code listing for the searching process of FIG. 2.

FIG. 7 is diagram illustrating a comparison of a subsequence (SEQ ID No. 3) within an input query sequence to a subject character sequence (SEQ ID No. 4).

FIG. 8 is a diagram illustrating an inaccurate scoring result. FIG. 8 shows hypothetical sequences SEQ ID Nos. 5-9.

FIG. 9 is a table of a scoring scheme for partial matches of nucleotides.

FIG. 10 is a diagram illustrating a superior scoring result obtained by the embodiment of FIG. 1. FIG. 10 shows hypothetical sequence SEQ ID Nos. 10-13.

FIG. 22 shows hypothetical sequence SEQ ID Nos. 14-15.

DETAILED DESCRIPTION

Figure 2:
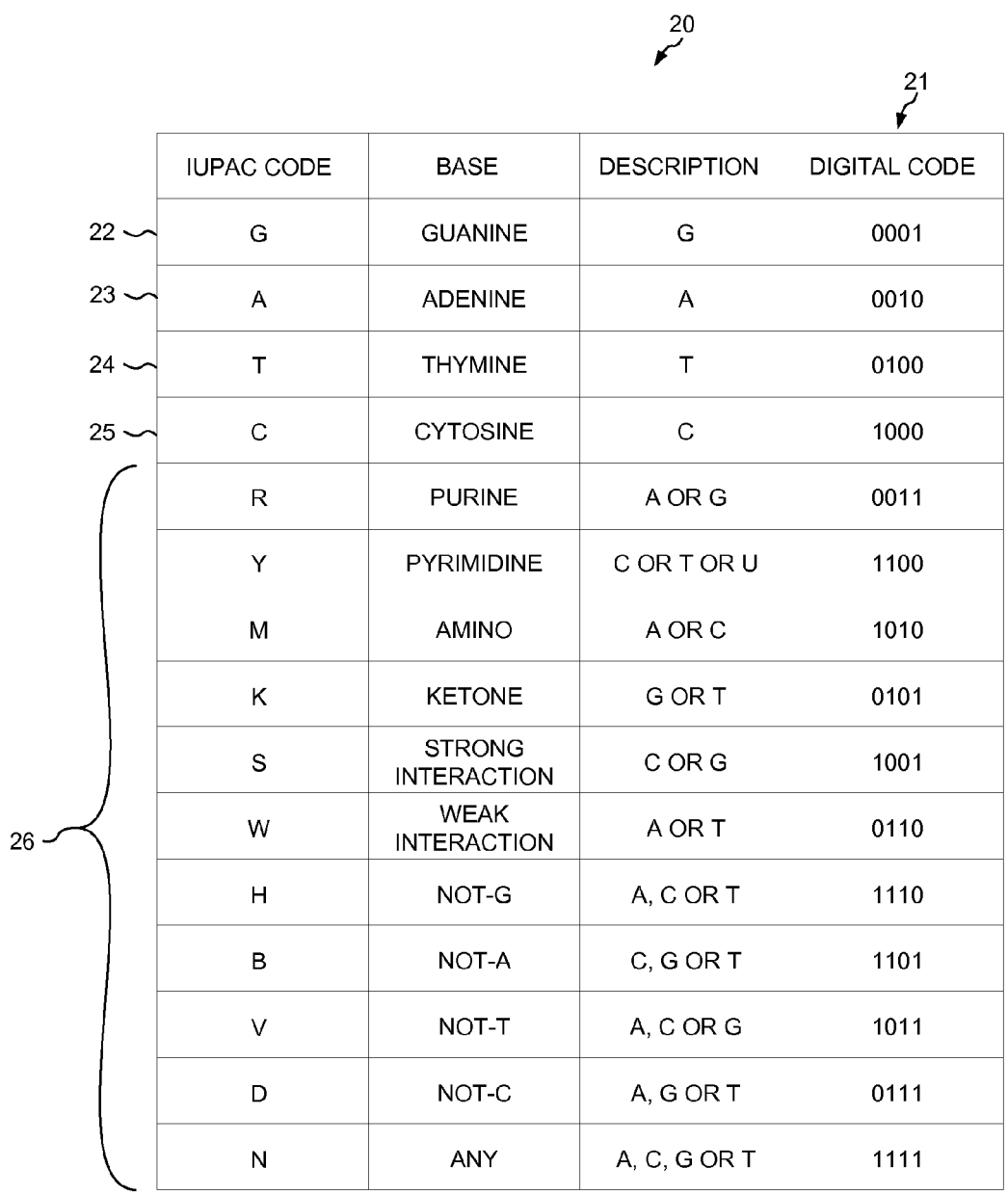
FIG. 2 is a table of a coding scheme suitable for use with the embodiment of FIG. 1.

Reference will now be made in detail to some embodiments of the invention, examples of which are illustrated in the accompanying drawings.

FIG. 1 is a high-level block diagram of a system 10 for implementing a method according to one embodiment of the present invention. System 10 includes both software and hardware and has a processor 11, a database 12 and an index 13 that is associated with the database 12. Processor 11 includes multiples components, including an indexing process 14, a searching process 15 and a scoring process 16. These processes may be software and/or hardware components. For example, indexing process 14 can be an index creation software module. System 10 indexes, identifies and retrieves from database 12 a database sequence 17 that is correlated to an input query sequence 18. In one example, input query sequence 18 represents a biological sequence, such as a DNA or protein sequence. Database sequences 17 also represents a biological sequence, such as a DNA or protein sequence, that is itself represented in a computer readable form. In this example, database sequence 17 represents a DNA sequence.

Database sequence 17 is a character sequence that is represented in a computer readable form. Each character included in database sequence 17 is represented using a suitable coding scheme such that each different character is represented using a different code. The character sequences in index 13 are also represented using the same codes.

In one example, index 13 stores a character sequence 19 having a corresponding subsequence in database sequence 17, together with information that identifies occurrences of each character sequence in database sequence 17. Each of character sequence 19, input query sequence 18 and database sequence 17 is represented using a coding scheme that facilitates rapid comparison of correlation between the sequences.

FIG. 2 illustrates a coding scheme of characters used in indexing and retrieving DNA sequences using one embodiment of the invention. A character set 20 is used to represent character sequence 19, input query sequence 18 and database sequence 17. Character set 20 includes digital codes 21 that are representative of each of the principle nucleotide bases 22, 23, 24, 25 (G, A, T and C) and eleven designating bases 26. For example, a sequence including the nucleotide bases "TACTACGGAAT" (SEQ ID No. 1) would be represented as "0100 0010 1000 0100 0010 1000 0001 0001 0010 0010 0100".

A one-hot coding scheme for digital codes 21 is employed for each of the principle nucleotides 22, 23, 24, 25 (G, A, T and C). This coding scheme is then extended to encode the fifteen official IUPAC_IUB single-letter base codes, using the resulting natural binary combination. As a consequence of this representation, the compatibility of any pair of digital codes 21 can be tested with a suitable binary operation (such as a binary AND operation). For example, H (not-G) AND Y (Pyrimidine bases: T or C or U) both allow T and C and therefore correlate because 1110 AND 1100=1100. Similarly, C and G do not correlate because 1000 and 0001=0000. Thus, a coding scheme of this type allows the present invention to detect such similarities in a computationally efficient manner.

Returning now to FIG. 1, index 13 identifies the occurrences of the corresponding subsequences using a suitable structure. In the present case, the structure includes a plurality of subindexes 27-30 wherein each of subindexes 27-30 is associated with a particular character sequence so that each subindex 27-30 contains a list of occurrences for a specific corresponding subsequence together with a subsequence description and boundary information for that corresponding subsequence. In this example, index 13 is divided into N subindexes of approximately 10-20 MB each for manageability.

FIG. 3 illustrates indexing process 14. Index 13 is constructed using indexing process 14. Index process 14 processes database sequence 17 so as to identify all sequential overlapping occurrences of k-tuple subsequences in database sequence 17 so as to create the index 13. Each k-tuple subsequence is a fixed-length, ordered sequence of characters that occurs in database sequence 17. For example, a k-tuple can be a unique sequence of eight nucleotide bases that occurs at least once in database sequence 17.

Figures 4, 5:
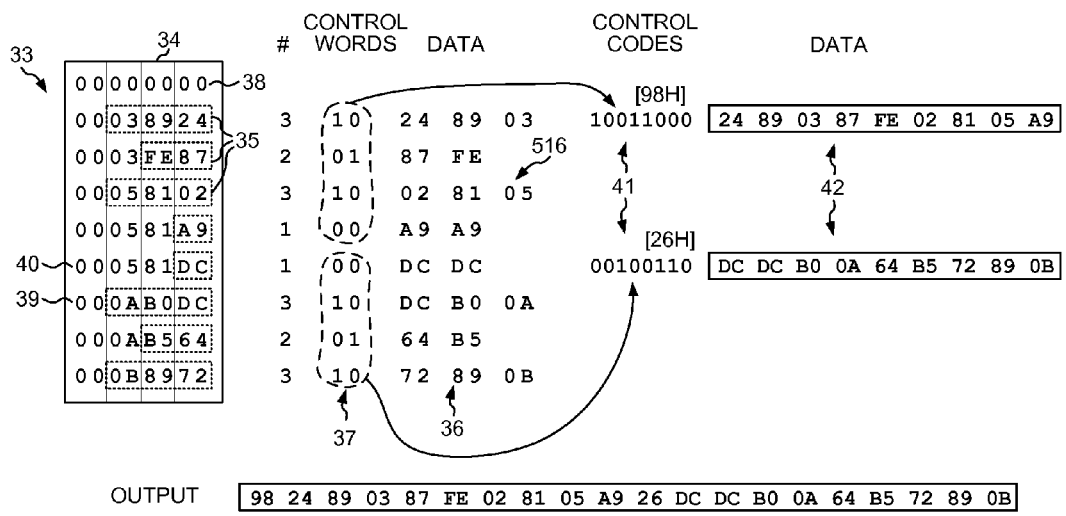
FIG. 4 is a diagram of sequentially overlapping 8-tuple subsequences as identified by the embodiment of FIG. 1.
FIG. 5 is a diagram illustrating an encoding scheme for compressing an index of the embodiment of FIG. 1.

FIG. 4 shows a method for identifying the occurrence of sequential overlapping 8-tuple subsequences within database sequence 17. FIG. 4 shows a portion 31 of database sequence 17. The identification of all sequential overlapping occurrences of 8-tuple subsequences entails incrementally (or "sliding") a window 32 having a length of 8-bases along database sequence 17 so as to identify all 8-tuple subsequences together with the corresponding address of each identified subsequence relative to the start of database sequence 17. FIG. 4 illustrates that window 32 is slid along database sequence 17 in one-base increments. In other embodiments of the method of FIG. 4, window 32 is slid by more than one base.

While or after identifying each sequential overlapping occurrences of 8-tuple subsequences, indexing process 14 creates one of subindexes 27-30 for storing occurrences of each instance of an 8-tuple subsequence. Each of subindexes 27-30 may store multiple occurrences because a particular subsequence, such as character sequence 19, may appear in database sequence 17 at plural positions. Accordingly, address information for each instance of a subsequence is stored in a corresponding subindex 27-30. Each created subindex 27-30 also stores a description of the subsequence and the boundaries of the subsequence. The address information may be represented using any suitable format. In the present case, an offset addressing format is employed that identifies the location of the beginning of a corresponding subsequence in database sequence 17 relative to the beginning of database sequence 17. The beginning of a subsequence is the address of the head cell, the first character of the subsequence.

The amount of information stored in index 13 is approximately an order of magnitude larger than that which is stores in database 12 itself. Thus, the information in index 13 is stored in a compressed form. In this example, the address information is compressed using a compression algorithm that reduces the size of index 13. The compression algorithm codes the address information substantially below entropy. Using a compression algorithm of this type is particularly advantageous because it substantially optimally compresses index 13.

To determine an appropriate compression algorithm, entropy characteristics can be gathered by indexing the Human Genome. For example, the entropy of the list of occurrences of any given 8-tuple in an index was found to be approximately 83% of original message length (OML), when representing occurrences as 32-bit unsigned integer absolute offsets. Using relative, as opposed to absolute, offsets reduces the entropy to approximately 70% of OML. By using absolute offsets and considering each byte position of the 32-bit values separately, the total entropy of each byte position was found to be approximately 67% of OML. This reflects the fact that the higher order bytes are much less likely to change than lower order bytes, which are increasingly random in distribution.

In this example, indexing process 14 employs a compression algorithm scheme for the address information in which two bits are used to indicate the number of differing bytes, beginning with the least significant. The bytes are then recorded after a two-bit length field. This results in a compressed message size approximately 59% of OML, substantially better than can be obtained by traditional entropy coding techniques. Furthermore, by coalescing the length fields into bytes, followed by the replacement bytes for each of the occurrences referred to by the length field byte, decompression can be achieved almost exclusively with byte aligned operations. This aids computational efficiency on general purpose computers. The entropy of the final compressed data stream was found to be approximately 99% of the compressed message length.

FIG. 5 shows an example of index compression. FIG. 5 illustrates how the above-described encoding scheme operates for eight occurrences of a particular tuple. In this example, offset addresses 33 are partitioned so as to provide a plurality of contiguous segments. Each of the offset addresses 33 is partitioned into four bytes. FIG. 5 shows a column with eight-digit hexadecimal values 34 that are representative of the successive offsets at which the particular tuple occurs relative to the start of database sequence 17.

Encoding consists of comparing each value with the one before (above) it to determine the minimum number of bytes beginning from the least significant (right most) that must be replaced. This is indicated by the bytes 35 in the dashed boxes. As is shown, only those segments that differ between successive addresses are stored. The differing segments 36 are shown in the column DATA. The differing segments 36 are stored together with control words 37 (shown here as binary control words) that indicate the number (#) of segments of each offset address that are stored. The encoding for the binary control words is: 00=1, 01=2, 10=3 and 11=4.

In this example, when the compression process begins, the offset of the first occurrence is set from an implied first address 38 of [00000000]. Note that for offset 39 (000AB0DC), the lowest byte (DC) is identical to the corresponding byte of the previous offset 40. Nevertheless, three bytes are replaced because the higher order bytes differ (that is, 0AB0 versus 0581).

Once the number of bytes that are to be replaced has been determined as indicated by the binary control words 37, binary control codes 41 are generated by combining the binary control words 37. In addition, byte streams 42 are constructed from the differing segments 36. Finally, this information is aggregated to form bytes of control codes 41 followed by associated replacement byte streams 42. This process is repeated for each four bytes of each offset, and then each control code and data stream is stored sequentially as the output. Thus, in this example, an input stream is compressed from 8×4=32 bytes to 20 bytes, including the two bytes (shown here as hex 98 and hex 26) of control codes 41.

Having described the components of an architecture that is suitable for performing indexing of character sequences, the description will now turn to the method itself The method is adapted to indexing genomic sequence alignments that typically consist of regions of high (close) homology interspersed with regions of low homology. This in some ways models the comparison and identification of protein super-families, where one or more functional domains exist in all members of a given super family. When applied to the genomic search process, the method first identifies all regions of very close homology. If such regions of close homology are assumed to not contain gaps, then they can be rapidly identified without the aid of an exhaustive dynamic programming search. The present invention performs this step efficiently using the index structures described above to identify all occurrences of each sequential, overlapping 8-tuple in database sequence 17.

In operation, processor 11 receives input query sequence 18 having a plurality of characters. A subsequence of input query sequence 18 is then compared with at least one character sequence obtained from the index 13. The comparison is performed by searching process 15 of processor 11. Each character sequence in index 13 has a corresponding subsequence in database sequence 17.

FIG. 6 illustrates the steps of a first task of finding alignment candidates, also called diagonals. In response to identifying a character sequence in index 13 having a correlation with an input query subsequence, searching process 15 uses information that identifies each occurrence of the corresponding subsequence in database sequence 17 to access an occurrence of the corresponding subsequence from database 12.

Each of these occurrences represents an alignment candidate. Searching process 15 then extends each alignment candidate in a non-gapped fashion to achieve a maximum scoring local alignment, referred to as an extended alignment candidate. This process is made more efficient through rapid comparison of sequence segments as described later. Finally, any extended alignment candidate having a score below some minimum threshold is discarded at this point.

Once a list of extended alignment candidates has been obtained, searching process 15 performs a joining procedure for each subsequence having multiple extended alignment candidates. This joining procedure differs from the FastA alignment process in that the exact dynamic programming score is calculated for the interalignment regions between extended alignment candidate. This is affordable due to the small area of each such region. Also, compatibility of extended alignment candidates is determined initially by considering the distance between them. Then as dynamic programming is performed, extended alignment candidates are removed that have a maximum dynamic programming score below some threshold. The score and path for the best join from each extended alignment candidate is recorded.

FIG. 6 illustrates a second task of joining nearby extended alignment candidates. At this point, there exists a list of extended alignment candidates and their dynamic programming scores, as well as the best paths between end points of extended alignment candidates that are joined through interalignment regions. This information allows extended alignment candidates to be assembled, and their exact dynamic programming score calculated, without any further dynamic programming effort. This is in contrast to both the FastA and NCBI-Blast alignment process, which both perform a constrained dynamic programming search of the region around an extended alignment candidate and do not fully utilize the information they have already obtained about the alignment.

The method of indexing and retrieving alignment sequences therefore also provides a method of amalgamating correlations between input query sequence 18 and a subsequence of database sequence 17 by using information previously obtained about an alignment. Hence, each subsequence of database sequence 17 that has a correlation with a subsequence of input query sequence 18 is identified, and a local alignment score is obtained for each identified subsequence.

Pairs of identified subsequences are then formed such that each pair is associated with a pair of subsequences in input query sequence 18. The subsequences of the pair of identified subsequences and subsequences of the associated pair are each separated by a corresponding interalignment region between the subsequences that has an arrangement of characters therein.

Different combinations of characters within the interalignment region between the pair of subsequences are compared with the interalignment region of the associated pair of subsequences so as to obtain a correlation score for each comparison. Having obtained a correlation score for each comparison, the identified pair and the combination of characters of the interalignment region of the identified pair with the maximum correlation score are then assembled to form an extended alignment candidate.

Joining regions of very close homology end to end, without considering alternative join paths that may deviate part way along a region of very close homology typically does not result in missing optimal extended alignment candidates. An optimal alternative alignment is unlikely to occur that involves a premature deviation from a very close homology alignment because the alternative alignment would introduce at least one penalty in leaving the existing alignment (i.e., a gap creation penalty) and would hence require a longer region of very close homology than the region lost through the deviation. In fact, for scoring systems where the gap creation and gap extension penalty are identical it can be shown that deviation will always result in a lower score.

Over all this approach results in a significant reduction in the direct dynamic programming time budget of the method. Indeed, typically less than 0.00001% of the potential dynamic programming space is evaluated, contributing less than 1% to the total execution time. The dominant remaining time expense (approximately 90%) becomes the identification of the extended alignment candidates. As a consequence, a number of techniques, can be applied to minimize the work of identifying extended alignment candidates by reducing the number of alignment candidates. It is envisaged that the amalgamating method is suitable for architectures that do not employ an index.

When performing dynamic programming expansion or alignment extension, the most desirable situation is when the two alignment candidates significantly concur, and without gaps. Determining when regions of this nature occur, and scoring them appropriately in a computationally efficient manner can be problematic, especially when matches between any of the fifteen IUPAC-IUB codes, as shown in FIG. 2, are allowed. A solution is to score a correlation between a subsequence of an input query sequence and a k-tuple character sequence. The correlation is scored using the above-described index structure, and the scoring is performed by scoring process 16.

The scoring method uses the above-described binary coding scheme representation to provide a first binary representation of a k-tuple subsequence of the input query sequence and represents the character sequence using the same binary coding scheme so as to provide a second binary representation. The method then performs a binary operation, including the first binary representation and the second binary representation so as to obtain a binary result that is able to be indexed into a lookup table. The lookup table associates a binary result for each possible pair of k-tuple subsequences with a value that is indicative of the number of congruent characters shared by the pair.

FIG. 7 illustrates the process of constructing lookup tables 43 to determine how many nucleotide bases match. Where the sequences are DNA sequences, the above-described 4-bit per base representation used by the present invention assists in this process. By performing a binary AND of any two nucleotide bases, it is possible to determine whether they match according to their IUPAC-IUB codes shown in FIG. 2. By constructing a 16-bit lookup table it is possible to determine, for a four-base region of the query and subject sequence, how many bases match.

When determining the dynamic programming score for a given local alignment, a second lookup table is also used to calculated the moderated dynamic programming scores for low complexity alignments, for example, where the subject sequence has a stream of N's. Such regions contribute nothing more than place holding to the alignment. If not treated appropriately, they can result in meaningless high scoring alignments. FIG. 8 shows a scoring alignment for a subject sequence of all N's. Alignments of varying specificity can be accommodated by the look up table.

FIG. 9 shows a reward scheme to score partial specific matches. Partially specific matches (for example, C vs S) may be rewarded a portion of the standard reward for a match, based on the probability of a match against them as approximated by counting the number of set bits in the 4-bit representation. Matches against N's are neither rewarded with a positive score nor penalized with a negative one.

Returning to FIG. 7, a partial match calculation is illustrates. FIG. 7 shows a dynamic programming calculation that applies rewards for partial specific matches. In the dynamic programming calculation of FIG. 6, the alignment of T vs N is given a score of zero, the specific base alignments +1 each, and the mis-match −3, resulting in a combined score of −1.

FIG. 10 shows an alignment moderated in this way, resulting in a 367 nucleotide exact alignment being more appropriately scored 332, due it is inclusion of 35 indiscriminate N bases. For scoring systems that work in bits of entropy, those scores can be looked up instead. Given modern computer memory and cache sizes, a 64 KB lookup table is of acceptable cost.

In one embodiment, index 13 has a maximum sub-index size of 20,000 sequences or 20,000,000 nucleotides, whichever is encountered first. A filtering threshold for the exclusion of frequent 8-tuples is set at 1.50 random expected frequency.

The method can be compared to the alignment process of NCBI-Blast 2.2.6 blastn. Both processes are executed in a single processor thread to allow direct comparison of the amount of work each process requires to perform a given search. The amount of work is measured in CPU seconds. Each process is required to perform the same 200 randomly selected queries against a draft of the human genome. The queries are obtained by randomly selecting 50-50,000 base sections from the human genome data, ignoring sequence boundaries. Only nucleotide-nucleotide searching is considered. The user space run time of each program is then recorded for later comparison. All tests are performed on a single processor AMD Opteron 1.4 GHz system with 1 MB cache and 1 GB of main memory running RedHat Linux 7.2 in 32 bit mode. The sensitivity of the method is measured relative to the Blast 2.2.6 nblast program. For each test case, the largest alignment from the first 100 sequences returned is compared. The percentage of each of hit that program B returned and that program A also identified, is summed to calculate the score for program A, and vice versa. Therefore a score of 100 is perfect.

The method has a speed advantage compared to Blast that is dependent on the query sequence length. The speed advantage of the method is greatest for shorter query sequences, especially below 500-1000 bp, where the speed advantage consistently exceeds an order of magnitude. This is particularly pertinent, as it is very common to search for queries with lengths below this bound. At the other extreme, the method's speed advantage decays to a mean of eight times faster than Blast.

Figure 11:
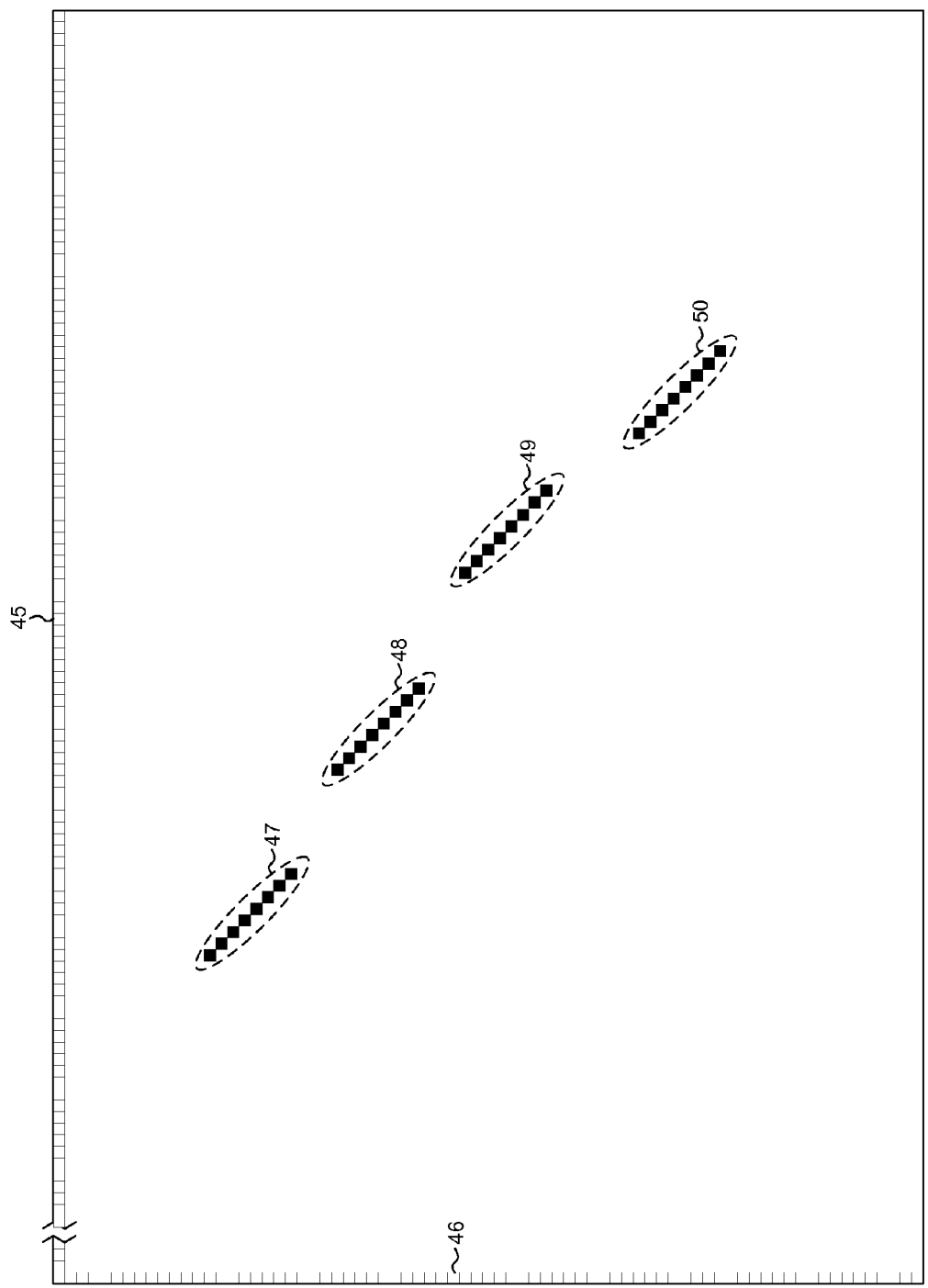
FIG. 11 is a diagram illustrating a method in accordance with one novel aspect.

FIG. 11 is a diagram of a method in accordance with one novel aspect. The row 45 of boxes extending across the top of the figure in the horizontal dimension represents a subject sequence of characters. Each box represents a character. The subject sequence may, for example, be a sequence of characters representing nucleic acids. The characters may be standard IUB/IUPAC nucleic acid codes. The column 46 of boxes extending down the left of the figure in the vertical dimension represents a query sequence of the same type of characters. A matrix of cells is formed. A blackened cell indicates a location where a character in the query sequence matches a character in the subject sequence.

Initially, the subject sequence is indexed. For each sequence of eight characters appearing in the subject sequence, the index contains a list of addresses. Each such address marks the starting place in the subject sequence where the occurrence of the eight-character sequence is found. A typical index entry for an eight-character sequence may have many addresses.

A query sequence is presented. It is desired to find corresponding portions of the subject sequence where a high degree of matching (homology) exists between the query sequence and the portion of the subject sequence. The query sequence is sectioned into eight-character sequences. For each of these eight-character sequences, the index is consulted and the associated addresses are extracted from the index. For each address (where an exact match is found between the eight characters of the query sequence and eight characters somewhere in the subject sequence), a corresponding sequence of blackened cells is illustrated in the matrix of FIG. 11. In FIG. 11, sequences 47-50 are illustrated. A matched sequence appears as a diagonal line of blackened cells and is called an "alignment." Each of the alignments of length eight in the figure is called an "alignment candidate" or "AC."

In FIG. 11, the only cells that are illustrated as blackened are cells of alignment candidates. There are, however, many additional characters in the query sequence that match other characters in the subject sequence. These matches, however, are not part of an alignment candidate of a length eight that was found in the index. The cells corresponding to these matches are, therefore, not illustrated as blackened in FIG. 11.

Next, an end extension process is performed on each of the alignment candidates in an attempt to convert each alignment candidate into what is called an "extended alignment candidate" or "EAC." An extended alignment candidate, in this example, must be of a predetermined length (for example, twelve cells on the diagonal) or more. In order to extend an alignment candidate, a rule is used. If two out of three cells extending in the diagonal direction being extended are matches (the query character in the row matches the subject character in the column), then the alignment candidate is extended in the direction of the diagonal. If two out of three cells are not matches, then the alignment candidate cannot be extended any longer.

An alignment candidate has a head (the upper leftmost cell of the alignment candidate) and a tail (the lower rightmost cell of the alignment candidate). The end extension process is performed on the head of each alignment candidate to extend the alignment up and to the left. The end extension process is performed on the tail of each alignment candidate to extend the alignment down and to the left. An alignment candidate becomes an "extended alignment candidate" only if the total length after end extension is twelve or more.

Figure 12:
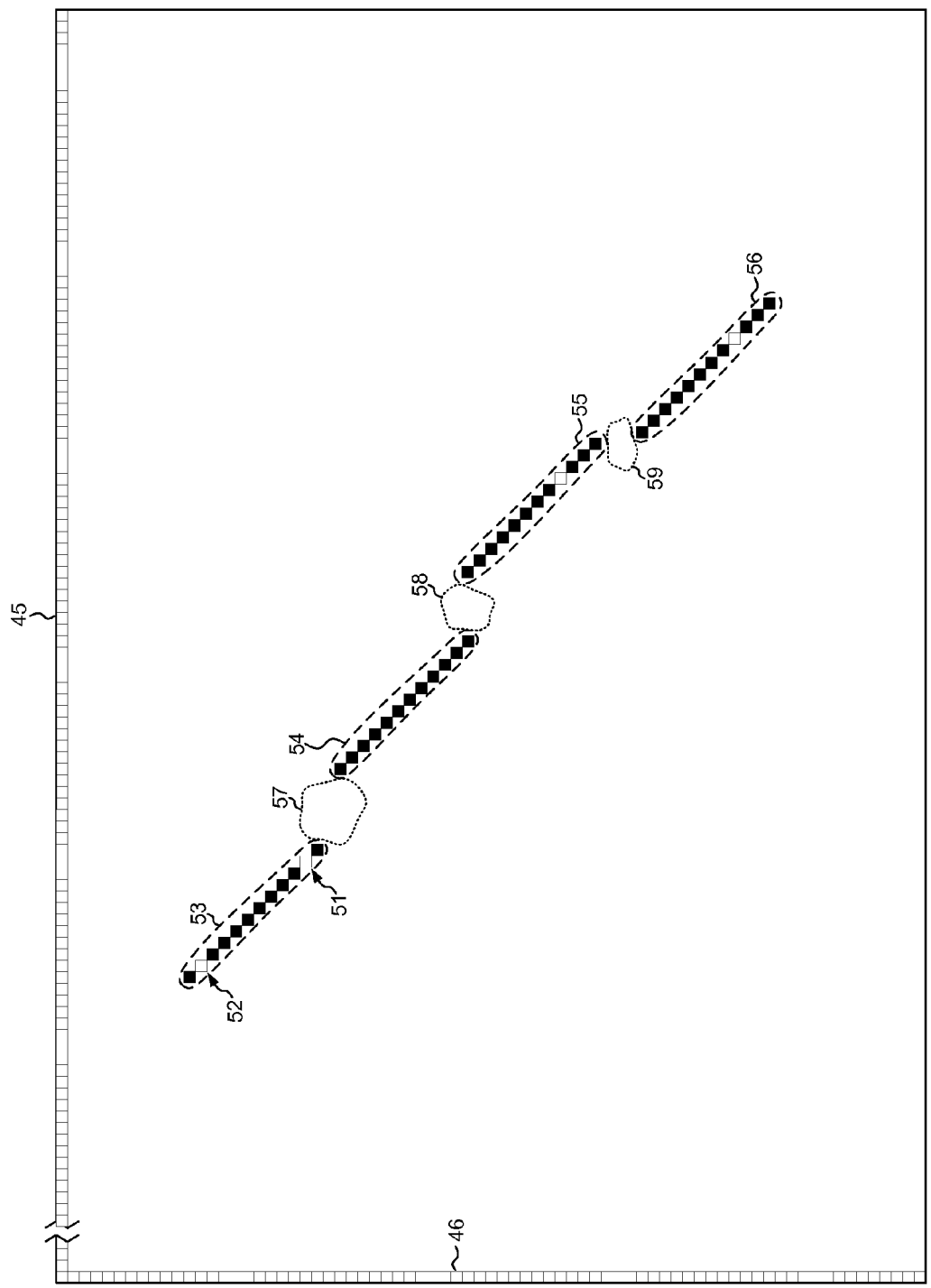
FIG. 12 is a diagram of the method of FIG. 11 showing alignment candidates.

FIG. 12 illustrates each of the alignment candidates of FIG. 11 after end extension. Alignment candidate 47 of original length eight was extended down and to the right two cells, and up and to the left two cells. Cells 51 and 52 represent non-matching cells. End extension was stopped in both diagonal dimensions once two of the last three cells were not matches. In the example of FIG. 12, the alignment candidates 47-50 of FIG. 11 are converted by the end extension process into extended alignment candidates 53-56, respectively.

Although a rule of two of the last three cells being a match is set forth above, other rules for when to stop the end extension process can be employed. For example, a scoring technique can be employed whereby the alignment candidate is extended in the diagonal direction until the accumulated score of the extended alignment drops below a predetermined threshold. Encountering a non-matching cell in the end extension may, for example, result in subtracting a predetermined amount from the accumulated score. Encountering a matching cell in the end extension may, for example, result in adding a predetermined amount to the accumulated score. Other scoring techniques can be applied as well.

Next, any alignment candidates that cannot be extended to be extended alignment candidates are ignored. Each of the remaining extended alignment candidates is scored. An extended alignment candidate can, for example, be scored starting in the upper leftmost cell of the extended alignment candidate (with any end extensions). That end cell is a match, so the starting accumulated score is a one. Then, proceeding down the alignment in a diagonal direction to the left, the accumulated score is added to or subtracted from depending on whether the next cell in the alignment is a match or a non-match. The result is a score for each extended alignment candidate. Each extended alignment candidate is then represented by a starting address (the location in the subject sequence where the leftmost cell of the extended alignment candidate is located), as well as the length of the extended alignment candidate and the score of the extended alignment candidate. Each extended alignment candidate has a head (the upper leftmost cell of the alignment) and a tail (the lower rightmost cell of the alignment).

In FIG. 12, there are four substantially co-linear extended alignment candidates 53-56. An interalignment region exists between each successive pair of the extended alignment candidates. In FIG. 12, there are three interalignment regions 57-59.

Figure 13:
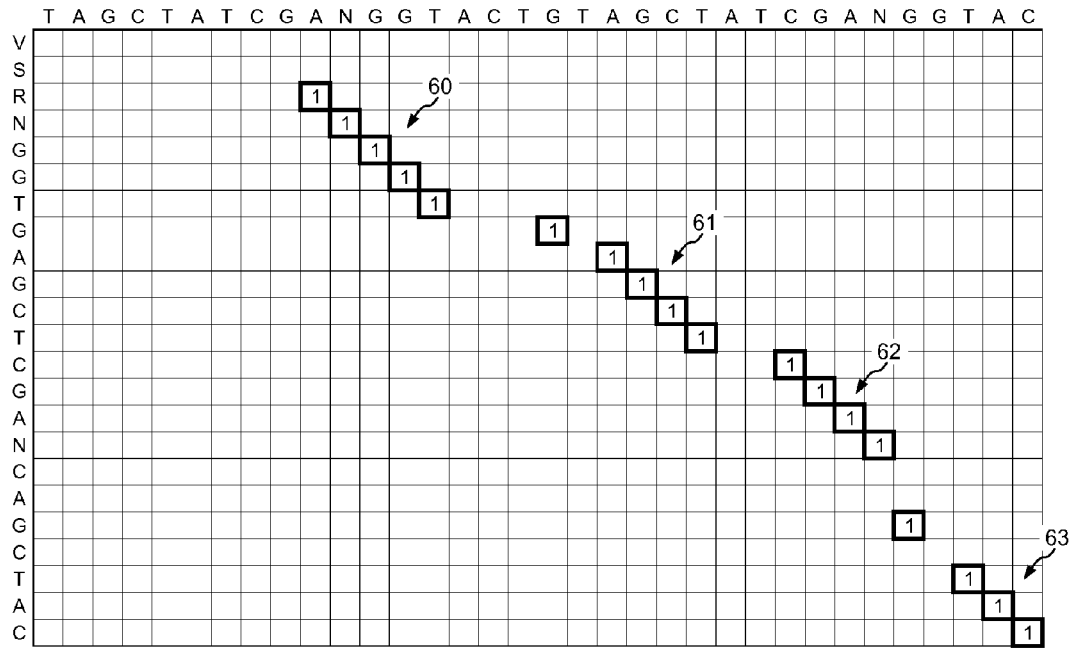
FIG. 13 is a diagram of the method of FIG. 11 showing four alignment candidates.

Next, dynamic programming is performed to score a path through each of the interalignment regions. FIG. 13 illustrates one way this can be done. In the example of FIG. 13, four extended alignment candidates 60-63 are illustrated. In the example of FIG. 13, an extended alignment candidate can be of length four. A "1" is illustrated in each of the cells of the extended alignment candidates to indicate a score of one. A score of plus one is the score for a match. Note that in this example, the end extension process did not result in any end extensions and each of the candidates 60-63 is shown as a contiguous diagonal of match cells. This situation is chosen to simplify the diagram and the explanation of the dynamic programming in an interalignment region.

Figure 14:
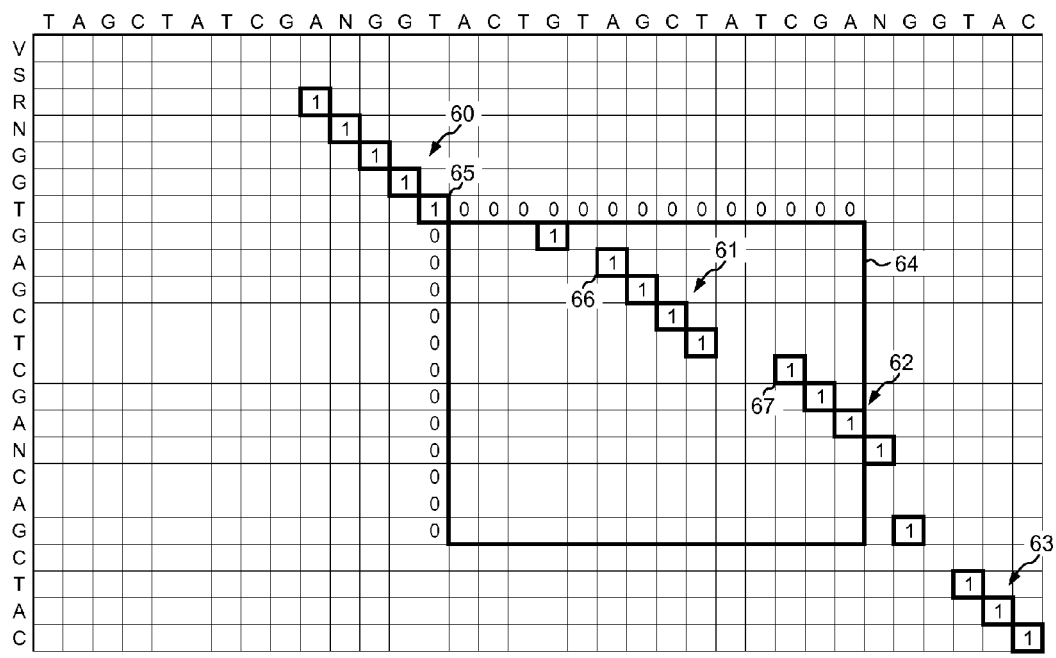
FIG. 14 is a diagram of the method of FIG. 11 showing head cells and tail cells of the alignment candidates.

In FIG. 14, extended alignment candidate 60 is first designated as the source alignment from which dynamic programming is to be performed. Dynamic programming is performed in a region 64 of predetermined size that extends downward and to the right from the tail 65 of source alignment 60. (In an example where end extension is performed, tail 65 would be the new tail after end extension.) In the present example, the predetermined size of region 64 is fourteen cells wide and twelve cells high. Note that the heads 66 and 67 of two extended alignment candidates 61 and 62 are found in region 64. These two extended alignment candidates 61 and 62 are designated as the destination alignments to which dynamic programming is to be performed.

Next, dynamic programming is performed starting in the upper leftmost cell of region 64. Scores are assigned to diagonal rows of cells in region 64. Each diagonal row of scored cells extends in a southwest-northeast direction. Diagonal row after diagonal row of cells are scored, proceeding toward the lower right corner of region 64. This dynamic programming only continues until a score is obtained for reaching the head of all the extended alignment candidates whose heads happen to be in region 64. Generally, dynamic programming does not have to be performed to many of the cells of region 64 because scores to the heads of the destination alignments are obtained before dynamic programming reaches those many cells.

Figure 15:
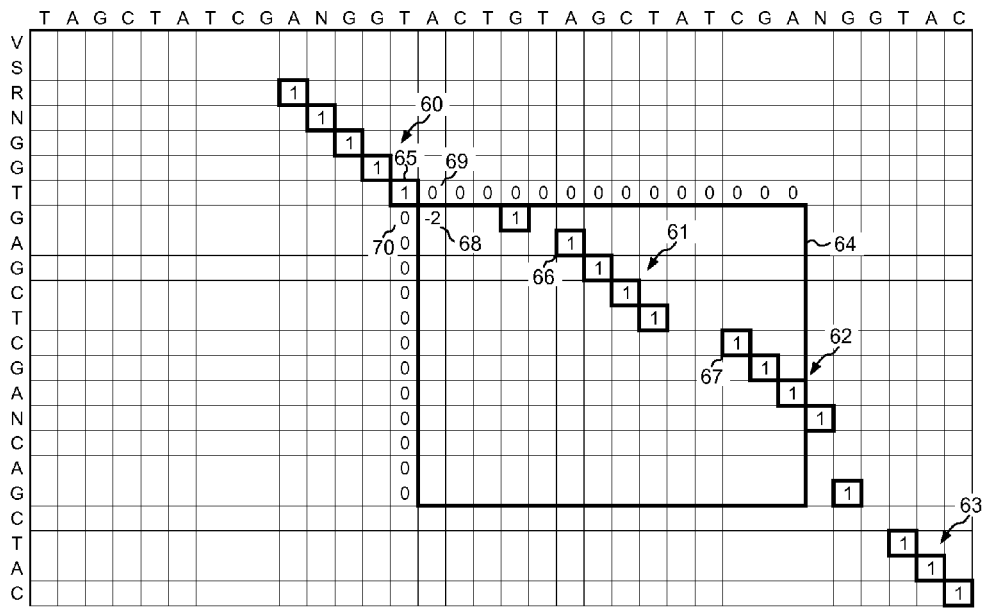
FIG. 15 is a diagram of the method of FIG. 11 showing a first step in dynamic programming a region adjacent to a tail cell.

FIG. 15 illustrates this dynamic programming in further detail. Initially, cells outside region 64 on the upper edge of region 64 and cells outside region 64 to the left of the left edge of region 64 are assigned scores of zero. The scores for all possible paths from the tail 65 of extended alignment candidate 60 to cell 68 are determined. The scoring is as follows: 1) When moving to the cell immediately below the current cell diagonally down and to the right, either a reward for match or a penalty for mismatch (also called a "hole") is applied. In one embodiment, the reward score is +1, and the penalty score is −3 (hole penalty). 2) When moving to a cell immediately below or to the right, a gap penalty is applied. In one embodiment, the gap penalty is −5. For each cell there are three choices for moving into it: diagonally down and to the right, below, or directly to the right. The movement that results in the highest score as described above is chosen. In other embodiments, different scoring systems may be used, as is understood by those skilled in the art.

One path is from the cell 69 above cell 68 down to cell 68. Cell 68 is a non-match cell. A gap penalty of five is subtracted from the initial score of zero from cell 69. Another path is from the cell 70 and to the right to cell 68. Cell 68 is a non-match cell. A gap penalty of five is subtracted from the initial score of zero from cell 70.

The last path is from tail 65 diagonally down and to the right to cell 68. Again, cell 68 is a non-match cell, and it is the first non-match into the region 64 from tail 65. A hole penalty of three is subtracted from the initial score of one from cell 65. Because the score of cell 65 was a one, the resulting score of minus two is the highest score of the tree paths. This minus two score is therefore shown recorded in cell 68 in FIG. 15.

Figure 16:
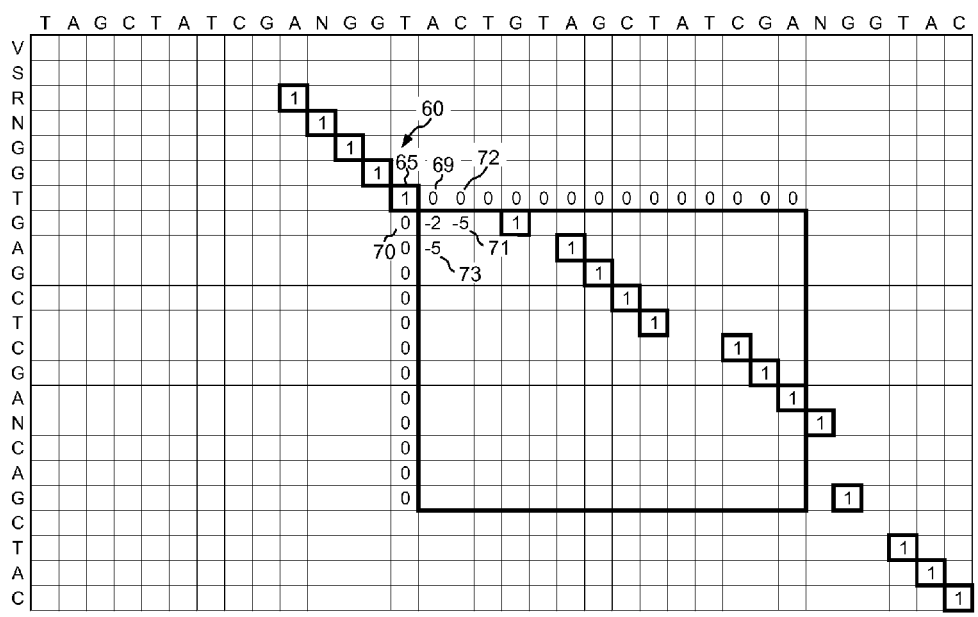
FIG. 16 is a diagram of the method of FIG. 11 showing additional calculations in dynamic programming of a region.

The same process is then applied to the next diagonal row of cells in region 64. This is illustrated in FIG. 16. Cell 71 is considered first. There are three paths into cell 71, one is from the top, one from the diagonal, and one from the left. In the case of the possible path down from cell 72, cell 71 would be the second non-match cell away from tail 65. A gap penalty of minus five is added to the score zero from cell 72.

In the case of the path diagonally from cell 69, cell 71 would again be the second non-match cell away from tail 65. A gap penalty of minus five is added to the score zero from cell 69.

In the case of the path to the right from cell 68, cell 71 is again the second non-match cell away from tail 65. A gap penalty of minus five is added to the score minus two of cell 68. The result would be minus seven.

Of the three paths into cell 71, minus five is the largest score. This minus five score is therefore recorded in cell 71 in FIG. 16. The score of cell 73 is determined in similar fashion.

Figure 17:
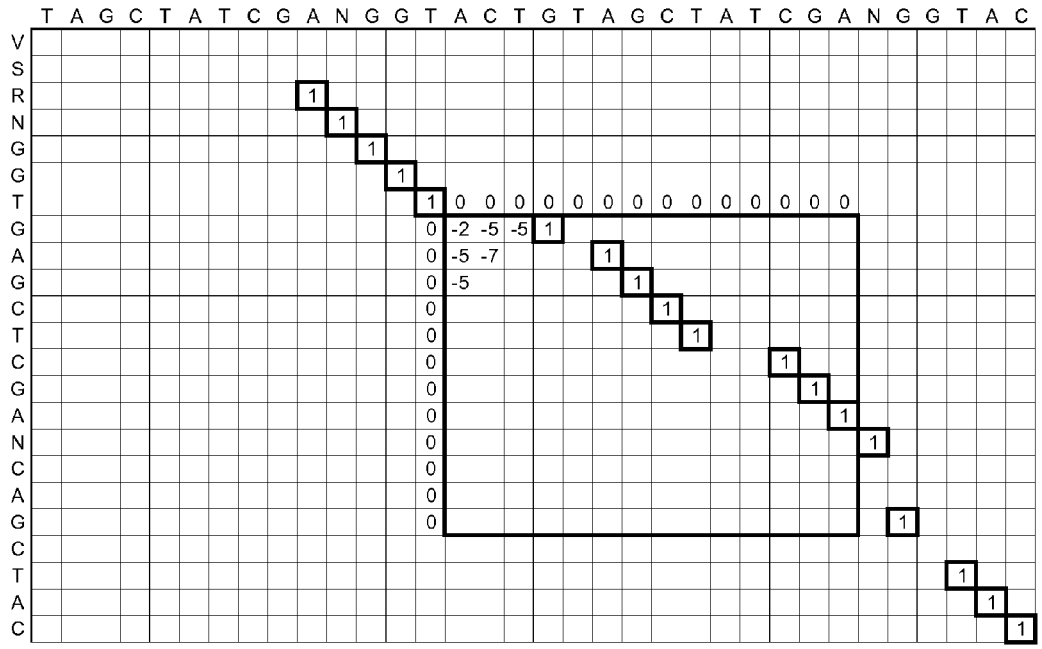
FIG. 17 is a diagram of the method of FIG. 11 showing calculations of a diagonal row of the region.

FIG. 17 shows the result of scoring the next diagonal row of cells of region 64.

Figure 18:
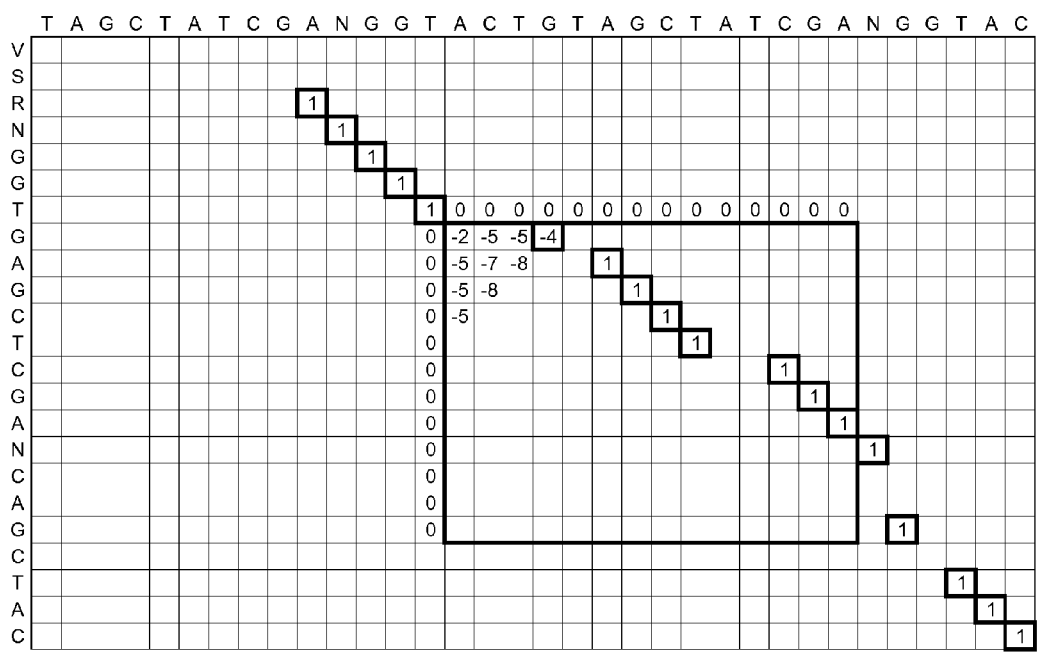
FIG. 18 is a diagram of the method of FIG. 11 showing calculations of the next diagonal row of the region.

FIG. 18 shows the result of scoring the next diagonal row of cells of region 64.

Figure 19:
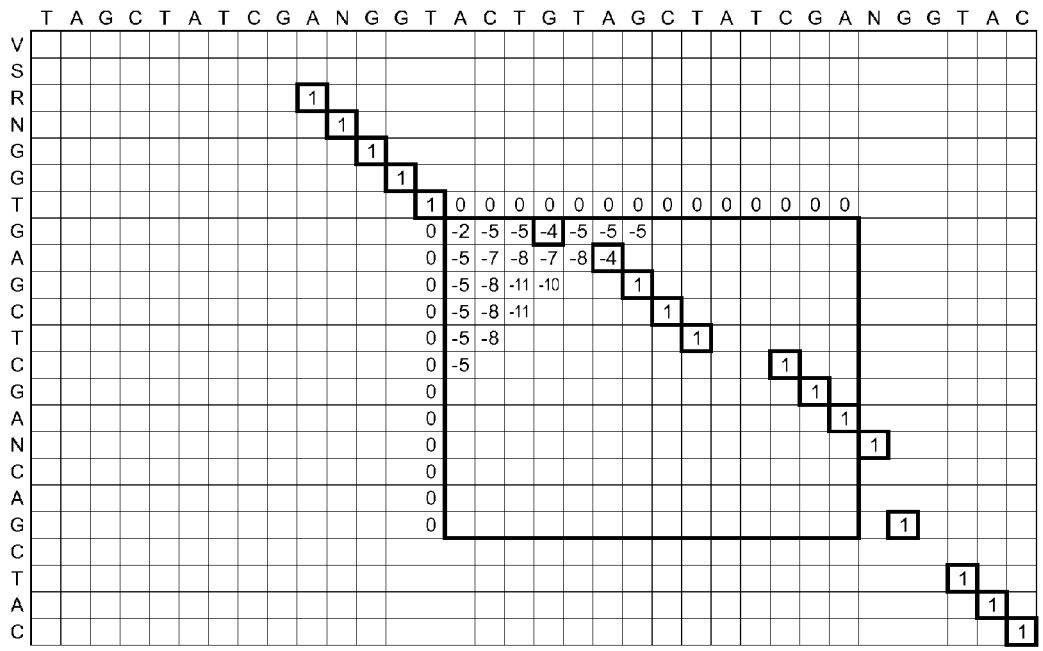
FIG. 19 is a diagram of the method of FIG. 11 showing calculations of yet another diagonal row of the region.

FIG. 19 shows the result of scoring the next diagonal row of cells of region 64.

Figure 20:
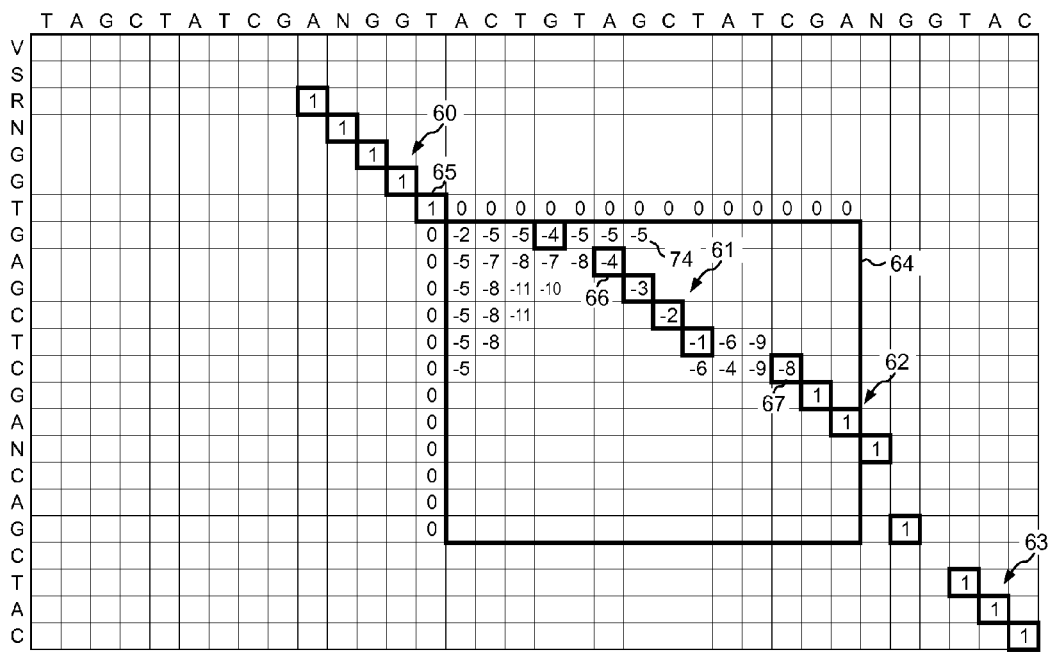
FIG. 20 is a diagram of the method of FIG. 11 showing the calculation of scores to the head cells of two alignments within the region.

FIG. 20 shows the result of scoring the first two cells in the next diagonal row of cells 74 and 66 of region 64. Note that a score of minus four is present in the cell 66 for the head of extended alignment candidate 61. The dynamic programming process has determined a score of minus four for a path from tail 65 of source extended alignment candidate 60 to the head 66 of destination extended alignment candidate 61.

There is, however, a head 67 of another extended alignment candidate within region 64. Dynamic programming therefore proceeds until a score is found for reaching head 67. In the present example, a score of minus eight is recorded in the cell 67 for the head of destination alignment 62. For clarification purposes, FIG. 20 does not show all the scores determined in order to reach head 67. Only the interesting scores are shown.

Next, a total score is determined for each of the destination alignments 61 and 62. The total score of a destination alignment is the sum of: 1) the score determined by dynamic programming from the tail of the source alignment to the head of the destination alignment, and 2) the score of the destination alignment itself.

Next, the total scores of the destination alignments 61 and 62 are compared. The destination alignment having the best total score is identified. In the present example, destination alignment 61 has a score of minus two for a total score of 4−2+4=6, and destination alignment 62 has a score of minus eight, for a total score of 4−8+4=0. Destination alignment 61 is therefore identified. The score generated by dynamic programming across the interalignment region is recorded.

Figure 21:
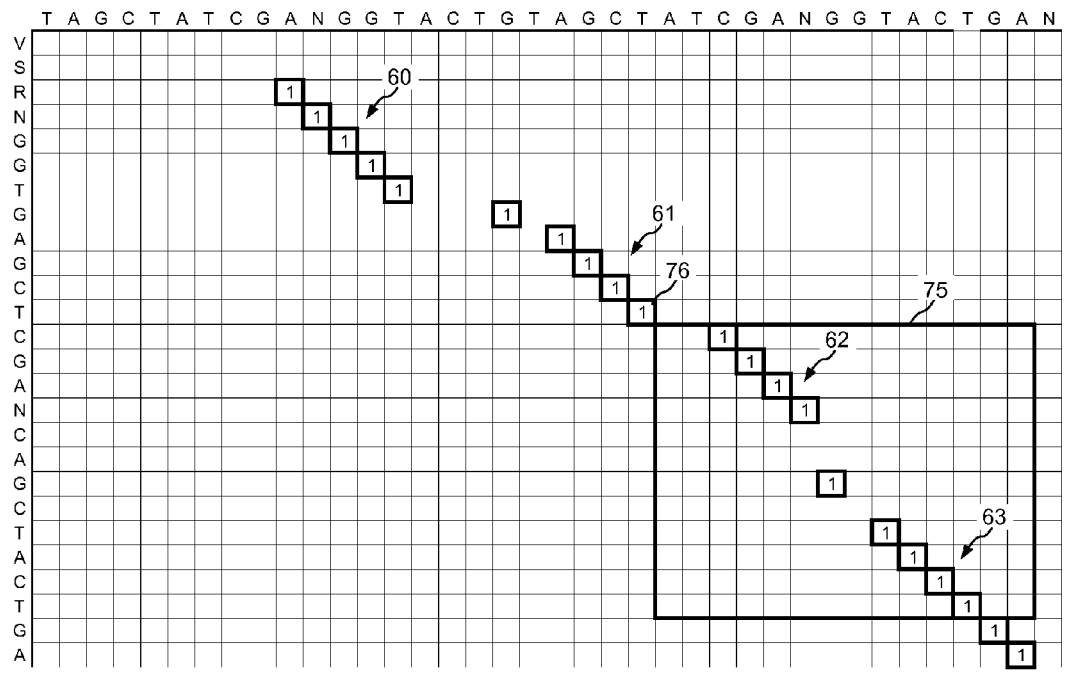
FIG. 21 is a diagram of the method of FIG. 11 showing calculations in dynamic programming of a second region.

The identified destination alignment 61 is identified as the source alignment and the process repeats. FIG. 21 illustrates alignment 61 as the new source alignment. A second region 75 of the predetermined size is shown extending from the tail 76 of alignment 61. Dynamic programming is performed in this second region 75 as described above. This process is repeated along the chain of alignments 60-63 until a score is determined for a path across each interalignment region.

Figure 22:
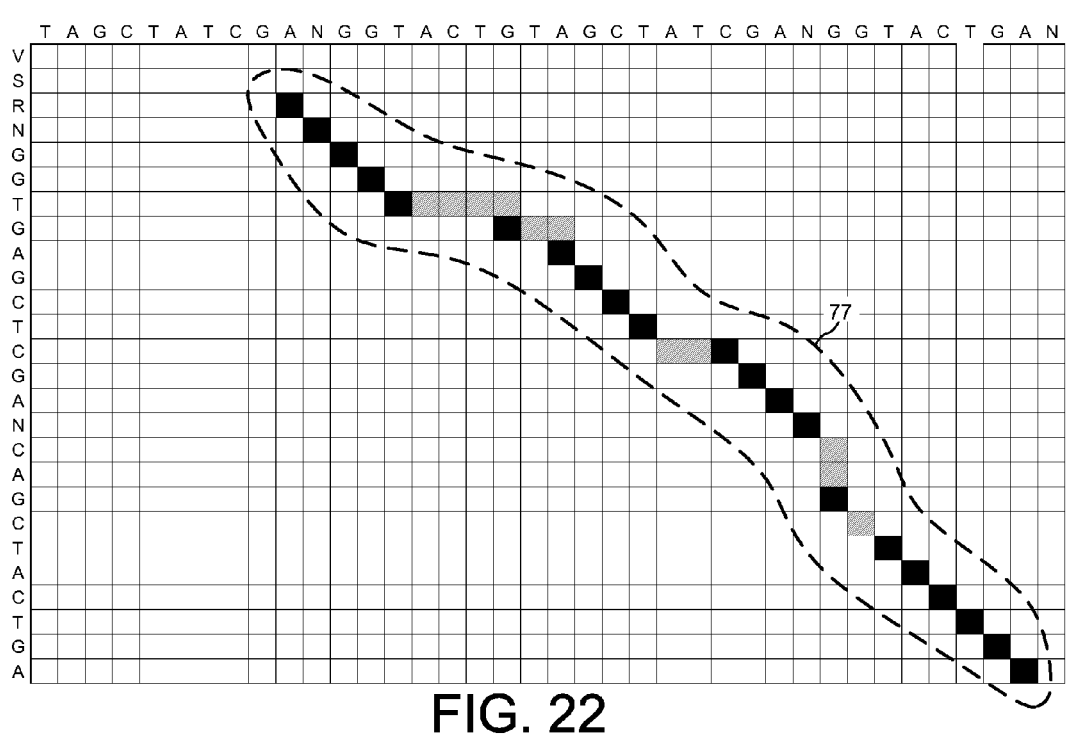
FIG. 22 is a diagram of the method of FIG. 11 showing a chain of alignments resulting from the best score from dynamic programming.

FIG. 22 illustrates the resulting chain 77 of alignments. Chain 77 is also called an "amalgamated alignment" or "AA." Each alignment in the chain has a score. The path across each interalignment region also has a score. In one embodiment, the scores for the alignments and the scores for the paths across the interalignment regions are summed. The resulting sum is the score for the chain. This process of generating a score for a chain of alignments is carried out for other chains of alignments, where each of the chains is for the same query sequence. The chains having the best chain scores are then identified. For each of these chains, the matching cells in the chain are displayed on a computer display along with the complete chain (the characters indicated in FIG. 22), the corresponding portion of the subject sequence, and the chain score.

Figure 23:
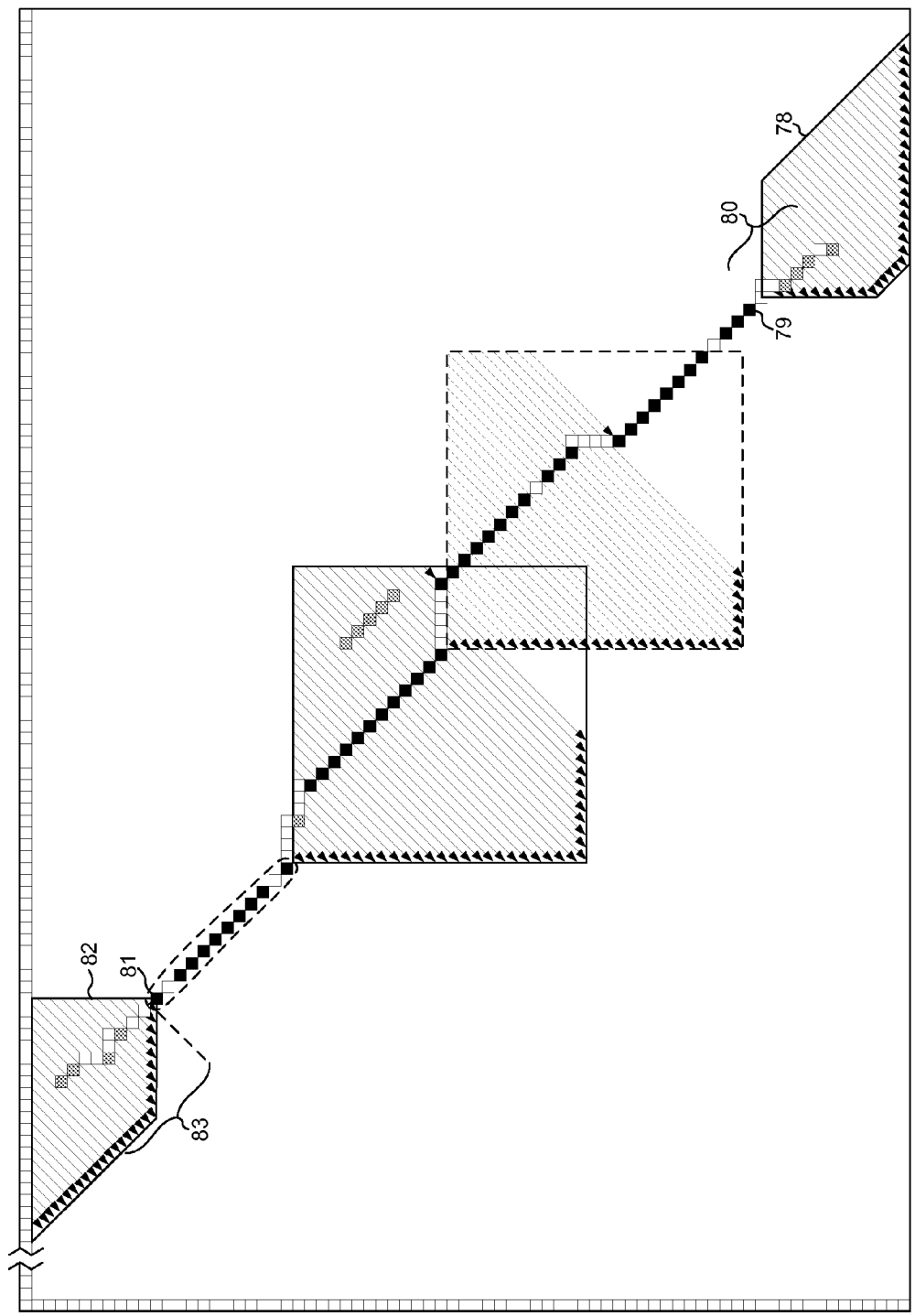
FIG. 23 is a diagram of the method of FIG. 11 showing dynamic programming in successive regions to obtain a dynamic programming tail extension score.

FIG. 23 illustrates a subsequent step in accordance with another embodiment. In the embodiment of FIG. 23, dynamic programming is performed in a banded region 78 starting at the tail 79 of the chain 77. Dynamic programming only proceeds as long as a predetermined condition is maintained. The score of this dynamic programming away from the tail 79 at the end of the chain 77 is called a "dynamic programming tail extension score". In one example, dynamic programming only proceeds as long as the score increases. The score may, for example, increase and then decrease. The maximum of the dynamic programming score is the "dynamic programming tail extension score". In the diagram of FIG. 23, the dynamic programming tail extension score is associated with tail extension 80. The path chosen by dynamic programming meanders off the diagonal to some extent.

In the same way that dynamic programming is performed away from the tail 79 of chain 77, so too is dynamic programming performed away from the head 81 of chain 77. In the case of head 81, dynamic programming extends upward and to the left within banded region 82. Dynamic programming only proceeds as long the predetermined condition is maintained. The score of this dynamic programming away from head 81 is called a "dynamic programming head extension score". In one example, dynamic programming only proceeds as long as the score increases. The maximum of the dynamic programming score is the "dynamic programming head extension score". In the diagram of FIG. 23, the dynamic programming head extension score is associated with head extension 83.

In the embodiment of FIG. 23, chain scores (without dynamic head and tail extension) are ranked. The chains with the best chain scores are then processed in accordance with the dynamic programming tail extension and dynamic programming head extension described above. For each chain, any dynamic programming tail extension score and any dynamic programming head extension score is added to the chain score. The extended chains are then ranked based on the enhanced chain scores. For each extended chain, the matching cells in the extended chain are displayed on a computer display along with the complete extended chain, the corresponding portion of the subject sequence, and the enhanced chain score.

Figure 24:
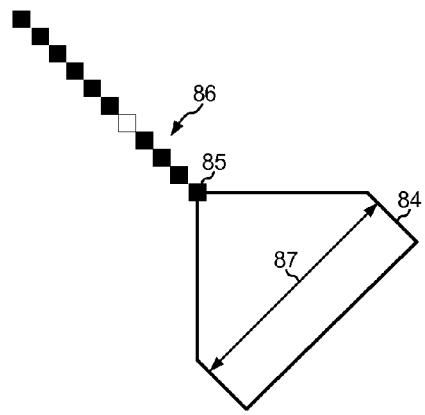
FIG. 24 is a diagram of the method of FIG. 11 illustrating dynamic programming in a banded region extending parallel from an alignment.

Although the region 64 of predetermined size in the above described methods is a rectangle, the region of predetermined size can be of other shapes. FIG. 24 is a diagram of one region 84 of predetermined size. Region 84 has a banded shape. Region 84 originates at the tail 85 of extended source alignment 86, and fans out to a width 87, and then extends further away from the origin with the constant width 87. Region 84 is said to be banded because it has two parallel sides that extend parallel to the source alignment 86.

Figure 25:
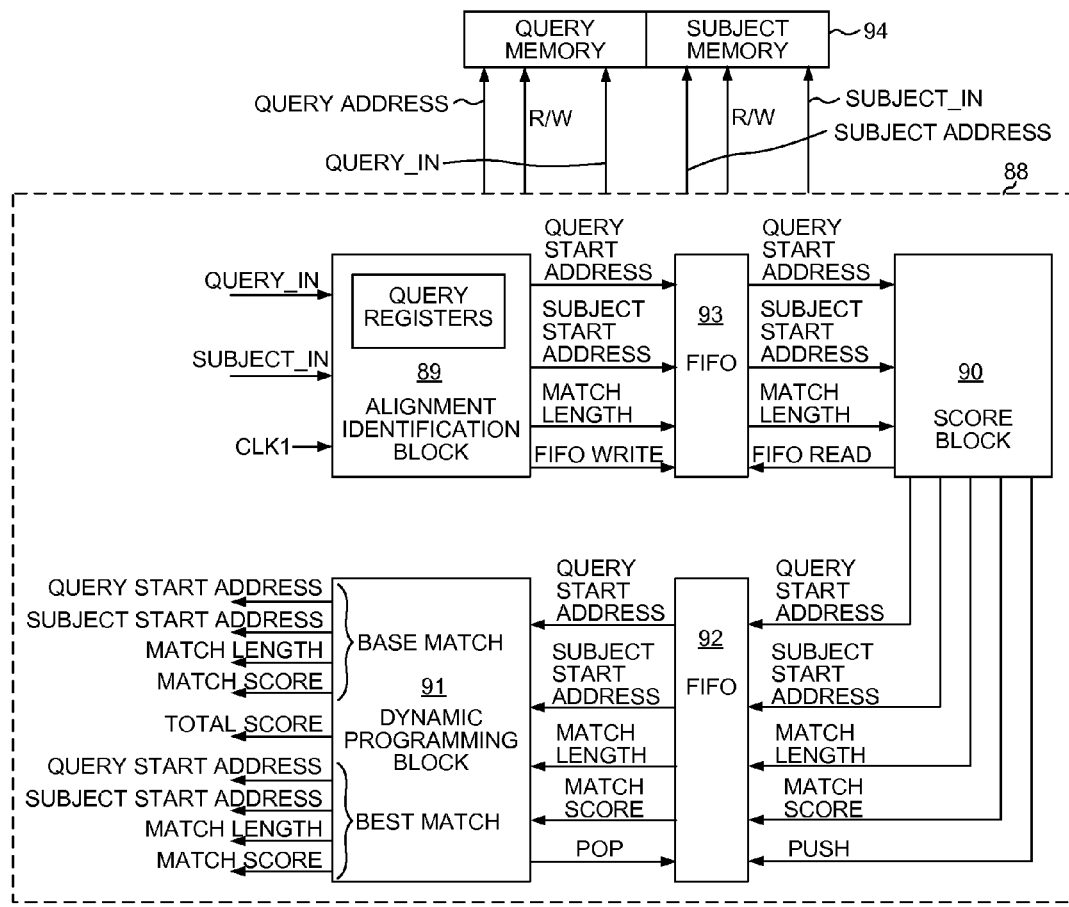
FIG. 25 is a high-level block diagram of an integrated circuit that performs dynamic programming and end extension according to the method of one embodiment.

FIG. 25 is a high-level block diagram of an integrated circuit 88. Integrated circuit 88 includes a block 89 that identifies alignments, a block 90 that scores alignments, a block 91 that performs dynamic programming and dynamic end extension, a stack 92, and a FIFO 93. A query sequence and a subject sequence are received onto integrated circuit 88 from external storage block 94. External storage may, for example, be a memory. The memory may be integrated onto integrated circuit 88 in certain embodiments.

The query sequence is received from block 94, is shifted into block 89, and is stored in block 89. The subject sequence is then received from block 94, and is shifted into block 89 past the query sequence so that every character in the query sequence is compared with every character in the subject sequence. In one example, an alignment starts when a string of matches starts and ends when a single non-match occurs at the end of the string. Identified alignments are recorded in FIFO 93. Each alignment is stored by identifying the head of the alignment (by query start address and subject start address) and the length of the alignment. This information is stored in FIFO 93.

Block 90 reads the alignment identification information from FIFO 93 and scores each successive alignment. The scoring process performed in block 90 is separated from the alignment identification process performed in block 90. There are relatively few scoring processes to be performed but each can be relatively involved and lengthy. The comparisons of the query sequence with the subject sequence are, on the other hand, relatively simple but must be done very rapidly. Separating the scoring process from the alignment identification process allows the alignment identification block 89 and the scoring block 90 to be clocked by different clock signals CLK1 and CLK2.

Scoring block 90 outputs an identification of each scored extended alignment candidate (query start address, subject start address, and length) as well as an alignment score. This information is pushed onto stack 92.

Dynamic programming block 91 pops stack 92, retrieves destination alignment identification information and associated scores. Dynamic programming block 91 then generates a score for the interalignment region from the source alignment to a destination alignment, generates an accumulated score (including the source alignment score, the interalignment score, and the destination score). The destination alignment then becomes the source alignment for the determination of the score of the next interalignment region. Dynamic programming block 91 repeats the process. When the interalignment score to the last destination alignment of the chain has been determined and added to the accumulated score along with the score of the last destination alignment, dynamic end extension is performed by block 91. The resulting score for the dynamic end extended chain (the total score) is output from integrated circuit 88 in parallel. Identification information (query start addresses and subject start addresses) for the various alignments within the corresponding chain are output from integrated circuit 88 in parallel, one at a time.

CD Appendix

The CD Appendix incorporated by reference from parent patent application Ser. No. 11/019,807 includes a hardware description (in VHDL hardware description language) of two versions of integrated circuit 88. One version is for detecting and scoring chains of alignments in protein character sequences. The other version is for detecting and scoring chains of alignments in DNA character sequences.

The CD appendix includes six directories. The directory "diag_match" is a hardware description for block 89 that finds alignments. There are two subparts to this directory, one is for including into the version of integrated circuit 88 for protein character sequences. The other subpart is for including into the version of integrated circuit 88 for DNA character sequences.

The directory "join_diags" is VHDL code for block 91 that performs dynamic end extension and dynamic programming. This directory has two subparts. One of the subparts is for a block to be included in the version of integrated circuit 88 for protein character sequences. The other is for a block to be included into the version of integrated circuit 88 for DNA character sequences.

The directory "score" is VHDL code for block 90 that scores alignments. The same VHDL description describes a single hardware block that is used in both the protein character sequence version of integrated circuit 88 as well as the DNA sequence version of integrated circuit 88.

The directory "test data" is a hardware description of the top-level of integrated circuit 88. The two directories "rams" and "packages" contain VHDL utility files. The directory "packages" contains the VHDL types used in both versions of integrated circuit 88 as well as VHDL constants and VHDL functions. The directory "rams" is a hardware description of the ram blocks, FIFO block 93 and stack 92.

A software driver executing on a host computer interfaces the host computer to integrated circuit 88. Integrated circuit 88 may, for example, be a configured field programmable gate array (FPGA) disposed on an expansion card. In such a case, the expansion card may be coupled to a bus (for example, PCI bus) on the motherboard of the computer. Suitable expansion cards carrying FPGAs are available from FPGA manufacturers. Customizable software drivers for interfacing application layer software to the expansion cards are also provided by FPGA manufacturers.

A user submits a query sequence via the host computer. The subject sequence to be searched is stored on the computer. The driver software causes the subject sequence and the query sequence to be supplied to integrated circuit 88. The "query sequence" is first shifted into the chip. The "subject sequence" is then shifted in character by character so that it passes the query sequence. Integrated circuit 88 performs the task of identifying a chain of alignments. The integrated circuit asserts an output flag high to indicate when an identification of a chain of alignments is available. The score for the chain is output. Identification of each alignment candidate of the chain is provided in parallel on output terminals of the integrated circuit along with a corresponding score. The software driver reads the chains of alignment candidates and their scores from the integrated circuit, and ranks them by score. The ranked results are displayed to the user on the monitor of the computer.

The CD Appendix also includes source code of a multiclient software embodiment for carrying out the scoring of chains of alignments. The system includes a central host computer and a plurality of client computers. The index of the subject sequence is broken up into a plurality of sub-indices. Each client computer stores one of the sub-indices. The same query sequence is sent to each of the client computers. The client computers send their outputs to the central host computer. In the case where a chain spans two sub-indices, the host computer assembles the scores reported by the appropriate client computers to form a chain score. In the case where the chain is fully matched with the sub-index on one client, then the client supplies the chain score to the host computer.

Although the present invention has been described in connection with certain specific embodiments for instructional purposes, the present invention is not limited thereto. Scoring techniques other than dynamic programming can be employed to generate scores for interalignment regions. Any scoring criteria can be used to score an interalignment region that supplies a score at least somewhat indicative of the quality of a path through the interalignment region. A very simple criteria such as the separation distance in non-matching cells in either the horizontal or vertical direction between adjacent alignments can, for example, be used. Discrete scores for all the alignments and all the interalignment regions of a chain need not be generated and then summed, but rather the sum can be generated by accumulating alignment and interalignment region scores in an accumulator as the joining process extends along the chain. The alignments of a scored chain need not be extended alignment candidates (EAC), but may also be alignments whose ends have not been extended. It should be noted that the present invention may be implemented in a variety of computer systems. The various techniques described herein may be implemented in hardware or software or a combination of both. Accordingly, various modifications, adaptations, and combinations of various features of the described embodiments can be practiced without departing from the scope of the invention as set forth in the claims.

What is claimed is:

1. A system for calculating scores of chains of sequence alignments of biological sequences, the system comprising:

an integrated circuit that receives a query sequence and a database sequence, the integrated circuit comprising:

a block that receives the query sequence;

a block that receives from an index a plurality of subsequences of the database sequence;

a block that identifies a plurality of alignment candidates of the query sequence;

a block that identifies a first chain of alignments and a second chain of alignments between the plurality of alignment candidates and the plurality of subsequences;

a block that scores the first chain of alignments and the second chain of alignments; and a block that performs dynamic programming in inter-alignment regions of the first chain of alignments and the second chain of alignments;

an end extension process converting the plurality of alignment candidates into a plurality of extended alignment candidates;

a joining process for joining the plurality of extended alignment candidates corresponding to the first chain of alignments and the second chain of alignments;

outputting a first chain score of the first chain of alignments and a second chain score of the second chain of alignments, wherein each of the first chain of alignments and the second chain of alignments is a plurality of substantially exact character matches between characters of the plurality of alignment candidates of the query sequence and characters of the plurality of subsequences of the database sequence and a plurality of paths through a plurality of interalignment regions; and a computer that receives the first chain score and the second chain score and that displays the first chain score and the second chain score.

2. The system of claim 1, wherein the first chain of alignments and the second chain of alignments are generated from the same query sequence.

3. The system of claim 1, wherein each of the first chain score and the second chain score is a sum of a plurality of alignment scores and a plurality of interalignment region scores.

4. A system for calculating scores of chains of sequence alignments of biological sequences, the system comprising:
   an integrated circuit that receives a query sequence and a database sequence, the integrated circuit comprising:
      a block that receives the query sequence;
      a block that receives from an index a plurality of subsequences of the database sequence;
      a block that identifies a plurality of alignment candidates of the query sequence;
      a block that identifies a first chain of alignments and a second chain of alignments between the plurality of alignment candidates and the plurality of subsequences;
      a block that scores the first chain of alignments and the second chain of alignments; and
      a block that performs dynamic programming in interalignment regions of the first chain of alignments and the second chain of alignments;
   an end extension process converting the plurality of alignment candidates into a plurality of extended alignment candidates;
   a joining process for joining the plurality of extended alignment candidates corresponding to the first chain of alignments and the second chain of alignments;
   outputting the first chain of alignments and the second chain of alignments, wherein each of the first chain of alignments and the second chain of alignments is a plurality of substantially exact character matches between characters of the plurality of alignment candidates of the query sequence and characters of the plurality of subsequences of the database sequence and a plurality of paths through a plurality of interalignment regions; and
   a computer that receives the first chain of alignments and the second chain of alignments and that displays the first chain of alignments and the second chain of alignments.

5. The system of claim 4, wherein the first chain of alignments and the second chain of alignments are generated from the same query sequence.

\* \* \* \* \*

SEQUENCE LISTING

```
<160> NUMBER OF SEQ ID NOS: 15

<210> SEQ ID NO 1
<211> LENGTH: 11
<212> TYPE: DNA
<213> ORGANISM: Artificial Sequence
<220> FEATURE:
<223> OTHER INFORMATION: A hypothetical sequence
```

```
<400> SEQUENCE: 1
tactacggaa t                                                          11

<210> SEQ ID NO 2
<211> LENGTH: 36
<212> TYPE: DNA
<213> ORGANISM: Artificial Sequence
<220> FEATURE:
<223> OTHER INFORMATION: A hypothetical sequence
<220> FEATURE:
<221> NAME/KEY: misc_feature
<222> LOCATION: (11)..(11)
<223> OTHER INFORMATION: n is a, c, g, or t

<400> SEQUENCE: 2
tagctatcga nggtactgta gctattagct atcctg                               36

<210> SEQ ID NO 3
<211> LENGTH: 19
<212> TYPE: DNA
<213> ORGANISM: Artificial Sequence
<220> FEATURE:
<223> OTHER INFORMATION: A hypothetical sequence

<400> SEQUENCE: 3
atcgtagctg atcgtgctg                                                  19

<210> SEQ ID NO 4
<211> LENGTH: 19
<212> TYPE: DNA
<213> ORGANISM: Artificial Sequence
<220> FEATURE:
<223> OTHER INFORMATION: A hypothetical sequence
<220> FEATURE:
<221> NAME/KEY: misc_feature
<222> LOCATION: (12)..(12)
<223> OTHER INFORMATION: n is a, c, g, or t

<400> SEQUENCE: 4
tagctgatcg anggtactg                                                  19

<210> SEQ ID NO 5
<211> LENGTH: 22
<212> TYPE: DNA
<213> ORGANISM: Artificial Sequence
<220> FEATURE:
<223> OTHER INFORMATION: A hypothetical sequence

<400> SEQUENCE: 5
tggcctgggc gaagagggag ag                                              22

<210> SEQ ID NO 6
<211> LENGTH: 22
<212> TYPE: DNA
<213> ORGANISM: Artificial Sequence
<220> FEATURE:
<223> OTHER INFORMATION: A hypothetical sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t
<220> FEATURE:
<221> NAME/KEY: misc_feature
<222> LOCATION: (18)..(22)
<223> OTHER INFORMATION: n is a, c, g, or t
```

-continued

```
<400> SEQUENCE: 6
tgncctgggc gnnnnntnnn nn                                              22

<210> SEQ ID NO 7
<211> LENGTH: 22
<212> TYPE: DNA
<213> ORGANISM: Artificial Sequence
<220> FEATURE:
<223> OTHER INFORMATION: A hypothetical sequence

<400> SEQUENCE: 7
attccccgag aaggaaaagg aa                                              22

<210> SEQ ID NO 8
<211> LENGTH: 22
<212> TYPE: DNA
<213> ORGANISM: Artificial Sequence
<220> FEATURE:
<223> OTHER INFORMATION: A hypothetical sequence
<220> FEATURE:
<221> NAME/KEY: misc_feature
<222> LOCATION: (1)..(22)
<223> OTHER INFORMATION: n is a, c, g, or t

<400> SEQUENCE: 8
nnnnnnnnnn nnnnnnnnnn nn                                              22

<210> SEQ ID NO 9
<211> LENGTH: 22
<212> TYPE: DNA
<213> ORGANISM: Artificial Sequence
<220> FEATURE:
<223> OTHER INFORMATION: A hypothetical sequence

<400> SEQUENCE: 9
tcctcagctc tcggcccatc gc                                              22

<210> SEQ ID NO 10
<211> LENGTH: 22
<212> TYPE: DNA
<213> ORGANISM: Artificial Sequence
<220> FEATURE:
<223> OTHER INFORMATION: A hypothetical sequence

<400> SEQUENCE: 10
aaattctggt gactggcata gg                                              22

<210> SEQ ID NO 11
<211> LENGTH: 22
<212> TYPE: DNA
<213> ORGANISM: Artificial Sequence
<220> FEATURE:
<223> OTHER INFORMATION: A hypothetical sequence

<400> SEQUENCE: 11
aacaatgtcg ccaaagccca tg                                              22

<210> SEQ ID NO 12
<211> LENGTH: 22
<212> TYPE: DNA
<213> ORGANISM: Artificial Sequence
<220> FEATURE:
<223> OTHER INFORMATION: A hypothetical sequence
<220> FEATURE:
<221> NAME/KEY: misc_feature
<222> LOCATION: (10)..(10)
<223> OTHER INFORMATION: n is a, c, g, or t
<220> FEATURE:
```

```
<221> NAME/KEY: misc_feature
<222> LOCATION: (20)..(20)
<223> OTHER INFORMATION: n is a, c, g, or t

<400> SEQUENCE: 12
cgtgaaagcn atgatttatn cc                                              22

<210> SEQ ID NO 13
<211> LENGTH: 11
<212> TYPE: DNA
<213> ORGANISM: Artificial Sequence
<220> FEATURE:
<223> OTHER INFORMATION: A hypothetical sequence

<400> SEQUENCE: 13
aagtgtcctg c                                                          11

<210> SEQ ID NO 14
<211> LENGTH: 38
<212> TYPE: DNA
<213> ORGANISM: Artificial Sequence
<220> FEATURE:
<223> OTHER INFORMATION: A hypothetical sequence
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 14
tagctatcga nggtactgta gctatcgang gtactgan                             38

<210> SEQ ID NO 15
<211> LENGTH: 26
<212> TYPE: DNA
<213> ORGANISM: Artificial Sequence
<220> FEATURE:
<223> OTHER INFORMATION: A hypothetical sequence
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 15
vsrnggtgag ctcgancagc tactga                                          26
```